United States Patent [19]

Kelkenberg et al.

[11] Patent Number: 5,023,018

[45] **Date of Patent: * Jun. 11, 1991**

[54] USE OF POLYHYDROXYALKYLAMINE-N,N-DICARBOXYLIC ACIDS AND THEIR SALTS AS BUILDERS IN DETERGENTS AND CLEANING AGENTS

[75] Inventors: Heike Kelkenberg, Gladbeck; Wulf Ruback, Recklinghausen, both of Fed. Rep. of Germany

[73] Assignee: Hüls Aktiengesellschaft, Marl, Fed. Rep. of Germany

[ * ] Notice: The portion of the term of this patent subsequent to Nov. 21, 2006 has been disclaimed.

[21] Appl. No.: 383,062

[22] Filed: Jul. 21, 1989

Related U.S. Application Data

[63] Continuation of Ser. No. 159,738, Feb. 24, 1988, Pat. No. 4,882,091.

[30] Foreign Application Priority Data

Mar. 27, 1987 [DE] Fed. Rep. of Germany ....... 3710062

[51] Int. Cl.$^5$ ......................... C11D 3/33; C11D 1/83; C07C 229/02

[52] U.S. Cl. ............................... 252/527; 252/174.19; 252/529; 252/546; 252/548; 252/DIG. 11; 560/170; 562/567; 562/568

[58] Field of Search ............... 252/548, 529, 527, 546, 252/174.19, DIG. 11; 560/170; 562/567, 568, 571

[56] References Cited

U.S. PATENT DOCUMENTS 2,868,724 1/1959 Zech .................................. 210/698
3,929,679 12/1975 Cala .................................... 252/527

FOREIGN PATENT DOCUMENTS 1011428 7/1957 Fed. Rep. of Germany .
2125249 11/1972 Fed. Rep. of Germany .
2177800 11/1973 Fed. Rep. of Germany .
0772820 4/1957 United Kingdom .

OTHER PUBLICATIONS

Majer, J., "Neue Komplexane. XXXVIII", Chem. Zvesti, vol. 34, No. 1 (1980), pp. 93-103.

Samoilova, O. I., "Compunds with Complexing Ability", Journal of Organic Chemistry of the USSR, vol. 8, No. 5, pp. 991-993.

Chem. Abstracts No. 14137g, vol. 54, No. 14, Jul. 25, 1960.

Chem. Abstracts No. 11618a, vol. 51, 1957.

*Primary Examiner*—Paul Lieberman
*Assistant Examiner*—Erin Harriman
*Attorney, Agent, or Firm*—Oblon, Spivak, McClelland, Maier & Neustadt

[57] ABSTRACT

Use of polyhydroxyalkylamine-N,N-dialkylcarboxylic acids or their salts, as builders for detergents and cleaning agents. Compounds of formula

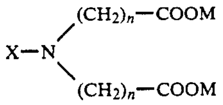

where X represents a polyhydroxyalkyl group with 3 to 7 carbon atoms and which may be glycosidically linked to a mono-, di-, or oligosaccharide; and n is 1 to 3, are used as builders for detergents and cleaning agents.

5 Claims, 2 Drawing Sheets

USE OF POLYHYDROXYALKYLAMINE-N,N-DICARBOXYLIC ACIDS AND THEIR SALTS AS BUILDERS IN DETERGENTS AND CLEANING AGENTS

BACKGROUND OF THE INVENTION

1. Field of the Invention

The invention is directed to the use of polyhydroxyalkylamine-N,N-dicarboxylic acids as builders in detergents and cleaning agents.

2. Discussion of the Background

The good detergency and cleaning capability of modern synthetic detergents is known to be due in large measure to their high content of sodium phosphate. Because of the hazard of eutrophication of surface waters, phosphates are being questioned from an environmental standpoint, and a progressive replacement of phosphates in detergents by substances which pose a lesser environmental threat has been required. The particular substitutes which have been employed include, most importantly, nitrilotriacetic acid, citric acid, polycarboxylic acids, and gluconic acid, as well as polymeric acids such as, e.g., polyacrylic acid, maleic acid copolymers, and polymaleic acid (see 1975 *Angew. Chem.*, 87, 115).

A major development is the use of inorganic waterinsoluble builders of type zeolite A (see Ger. AS 24 12 837) which are considered excellent in environmental safety but which do not provide adequate support for the washing action of the surfactants, and can only be used in combination with one of the abovementioned organic builders as a phosphate substitute.

Thus it is seen that there is still no phosphate substitute for use in detergent formulations which has characteristics parallel to the excellent combination of characteristics of sodium triphosphate as a builder.

SUMMARY OF THE INVENTION

Accordingly, one object of the present invention is to provide a detergent builder which has characteristics comparable to sodium triphosphate.

This and other objects which will become apparent from the following specification have been achieved by the use of polyhydroxyalkylamine-N,N-dialkylcarboxylic acids or their salts, of formula I:

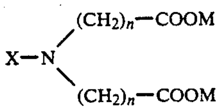

(I)

where

X represents a polyhydroxyalkyl group which has 3 to 7, preferably 4 to 6 carbon atoms and which may be glycosidically linked to a mono-, di-, or oligosaccharide;

M represents hydrogen, ammonium or an alkali metal ion; and n is an integer from 1 to 3, as builders for detergents and cleaning agents.

DETAILED DESCRIPTION OF THE PREFERRED EMBODIMENTS

Figure 1:
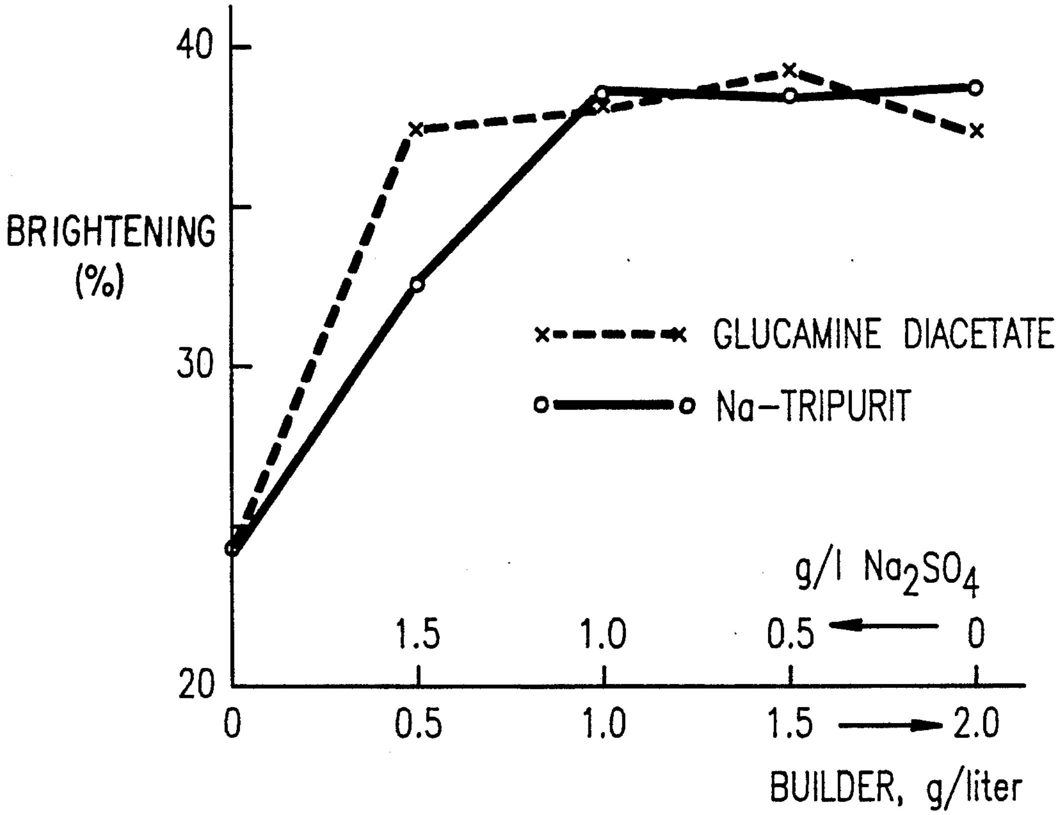

The inventively employed polyhydroxyalkylamine-N,N-dialkylcarboxylic acids or their salts should be present in an amount of 2–60 wt.%, preferably 5–25 wt.%, based on the total weight of the detergent or cleaning agent mixture.

M may be hydrogen, lithium, sodium, potassium, or ammonium, preferaoly sodium, n is preferably 1. X may represent the following polyhydroxyalkyl groups: 1-deoxyerythrityl, 1-deoxyarabltyl, 1-deoxyxylityl, 1-deoxysorbityl, 2-deoxysorbit-2-yl, 1-deoxymannltyl, 2-deoxymannlt-2-yl, 1-de oxygaiactityl, 1-deoxy -4-glucosido-sorbityl, 1-deoxy-4-galactosido-sorbityl, 2-deoxy-4-glucosido-sorbit-2-yl, 2-deoxy-4-glucosido-mannit-2-yl, 1-deoxy-4-malto-glucosido-sorbityl, 1-deoxy-4-oligoglucosido-sorbityl, or 1-deoxy-4-polyglucosido-sorbityl. Preferably, X represents a 1-deoxysorbityl group.

The following compounds are examples of builders which may be employed according to the invention: glucamine diacetate, erythramine diacetate, arabinamine diacetate, xylamine diacetate, mannamine diacetate, galactamine diacetate, 2-deoxy-.sorbit-2-ylamine diacetate, 2-deoxy-mannit-2-ylamine diacetate, 4-glucosido-glucamine diacetate, 4-galactosido-glucamine diacetate, 2-deoxy-4-glucosido-sorbit-2-ylamine diacetate, 2-deoxy-4-glucosido-mannit-2-ylamine diacetate, 4-malto-glucosido-glucamine diacetate, 4-oligo-glucosido-glucamine diacetate, and 4-polyglucosido-glucamine diacetate.

The following are examples of surfactants which may be present in the detergent or cleaning agent: (a) anionic surfactants, e.g. alkylarylsulfonates, particularly alkylbenzenesulfonates; olefinsulfonates, sec-paraffinsulfonates; sulfosuccinic acid half ester salts; or fatty alcohol ether sulfates; (b) nonionic surfactants, e.g. fatty alcohol polyglycol ethers, alkylphenol polyglycol ethers, fatty acid polyglycol esters, or polypropylene oxide-polyethylene oxide mixed polymers; etc.

The compounds of general formula I are known per se. See Ger. AS 10 11 428, wherein a method of preparing the compounds is described along with their use as therapeutic agents. According to the method described, the compounds may be prepared by carboxyalkylation of the corresponding polyhydroxyalkylamines, or by polyhydroxyalkylation of the corresponding iminodi-(alkylcarboxylic) acids.

The polyhydroxyalkylamine-N,N-dimethylcarboxylic acids

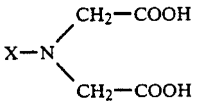

may be prepared, for example, by treating the corresponding polyhydroxyalkylamines with formaldehyde and hydrocyanic acid, or by carboxymethylation with chloroacetic acid and sodium hydroxide.

The polyhydroxyalkylamines may be prepared by the generally known method of reductive amination of sugar derivatives with liquid ammonia. The following are examples of preferred sugar derivatives: erythrose, glucose, galactose, mannose, fructose, arabinose, xylose, maltose, saccharose, lactose, cellobiose, maltotriose, maltodextrin, and other starch byproducts (e.g. glucose syrup).

The excellent action of the builder sodium triphosphate in synthetic detergents and cleaning agents is very complex. The most important criteria are as follows: (a)

good complex-forming ability with calcium and magnesium ions; (b) synergistic influence of the primary detergent action of synthetic anionic and nonionic surfactants and soaps; (c) good antiredeposition power for soils, and good dissolution power for soil particles; (d) good compatibility with other builders, e.g. sodium silicate and sodium sulfate; (e) no effect on perborate stability; and (f) inhibition of deposition of inorganic insoluble salts onto the fabric (incrustation).

The inventively employed alkali salts of polyhydroxyalkylamine-N,N-dialkylcarboxylic acids fully satisfy these criteria.

Other features of the invention will become apparent in the course of the following description of exemplary embodiments which are given for illustration of the invention and are not intended to be limiting thereof.

The invention will now be illustrated in more detail in the following, using the example of glucamine-N,N-diacetate shown below.

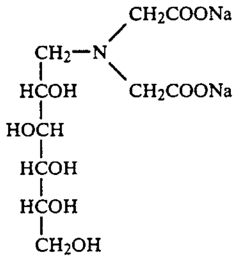

EXAMPLES

Preparation of Glucamine-N,N-diacetate 181 g (1 mol) D-glucamine and 194 g (2.05 mol) chloroacetic acid were stirred with 50 ml water at 40° C., to form a suspension, to which 164 g (2.05 mol) 50% sodium hydroxide was added slowly. The reactant mixture at this point had a pH of less than 8.5. At 55° C. the material comprises a clear solution. An additional 164 g NaOH solution was added gradually at a pH of 8 to 9, over a period of 2 hours. Stirring was continued an additional 30 minutes at 70° C. After cooling, 58g NaCl was filtered out. The filtrate had the following composition:

48.7% Glucamine-N,N-diacetate
1.6% Hydroxyacetate
8.6% NaCl
41.0% Water.

The pH of the final solution was 10.3. This solution was used as a test solution for the following application tests.

In all cases, sodium triphosphate (Na-Tripurit ®, supplied by Hoechst) was used as a comparison material.

In the washing test, the inventively employed material was combined with the anionic surfactant alkylbenzenesulfonate (Marlon A ®, supplied by Huels). In some instances, zeolite (Sasil ®, supplied by Degussa) was included as a comparison material.

Calcium Binding Capability According to Hampshire Test 2 g of the test substance was dissolved in 90 ml water, and 10 ml of a 2% sodium carbonate solution was added. After bringing to temperature (see Table), the solution was titrated at pH 10 with a 4–5% calcium acetate solution until a distinct and persistent turbidity was present.

TABLE 1

HAMPSHIRE TEST

| Temperature (°C.) | Ca binding capability (mg $CaCO_3$/g substance) Glucamine diacetate | Na-Tripurit ® |
|---|---|---|
| 20 | 224 | 163 |
| 60 | 197 | 120 |
| 90 | 146 | 84 |

Detergency in Combination with Marlon A ®

Laboratory washing machine: Linitest ® (supplied by Heraeus).
Test fabric: Standard soiled cotton (supplied by WFK, Krefeld).
Brightening measured against standard white (MgO), by a UV spectromerer (Beckmann "DK 2A").
Hardness of water: 13° dH.
Washing time and temperature: 30 min, 90° C.
Bath ratio: 1:70.

Concentration of the agents in the bath: 1 g/liter Marlon A ®+2 g/liter builder.

TABLE 2

DETERGENCY

| Builder | Brightening (%) 1st washing | 2nd washing |
|---|---|---|
| Glucamine diacetate | 30.3 | 37.4 |
| Na-Tripurit ® | 32.7 | 37.4 |
| Sasil ® | 21.5 | 31.1 |
| Sasil ® + 10% glucamine diacetate | 23.9 | 35.1 |

Incrustation

Following a 3rd washing, the fabric was incinerated at 600° C., 2 hours. The ash percentage was taken as a measure of incrustation.

TABLE 3

INCRUSTATION

| Builder | Ash (wt. %) |
|---|---|
| Control test* | 0.83–0.85 |
| Glucamine diacetate | 0.57–0.57 |
| Na-Tripurit ® | 0.26–0.26 |
| Sasil ® | 0.88–0.94 |
| Sasil ® + 10% glucamine diacetate | 0.82–0.97 |

*For comparison, the value without addition of surfactant and builder, in drinking water, is given.

Detergency in Combination with n-Dodecylbenzene-sulfonate (Marlon A ®) and Sodium Sulfate FIG. 1 is a graph of brightening versus builder content in detergent formulation. Concentrations of agents in bath: 0.75 g/liter Marlon A ®+up to 2 g/liter builder. The amount of builder was steadily replaced by increasing amounts of sodium sulfate. However, the total amount of sodium sulfate+builder in all samples was constant at 2 g/liter.

Perborate Stability in the Presence of Fe(III) at 60° C.

Figure 2:
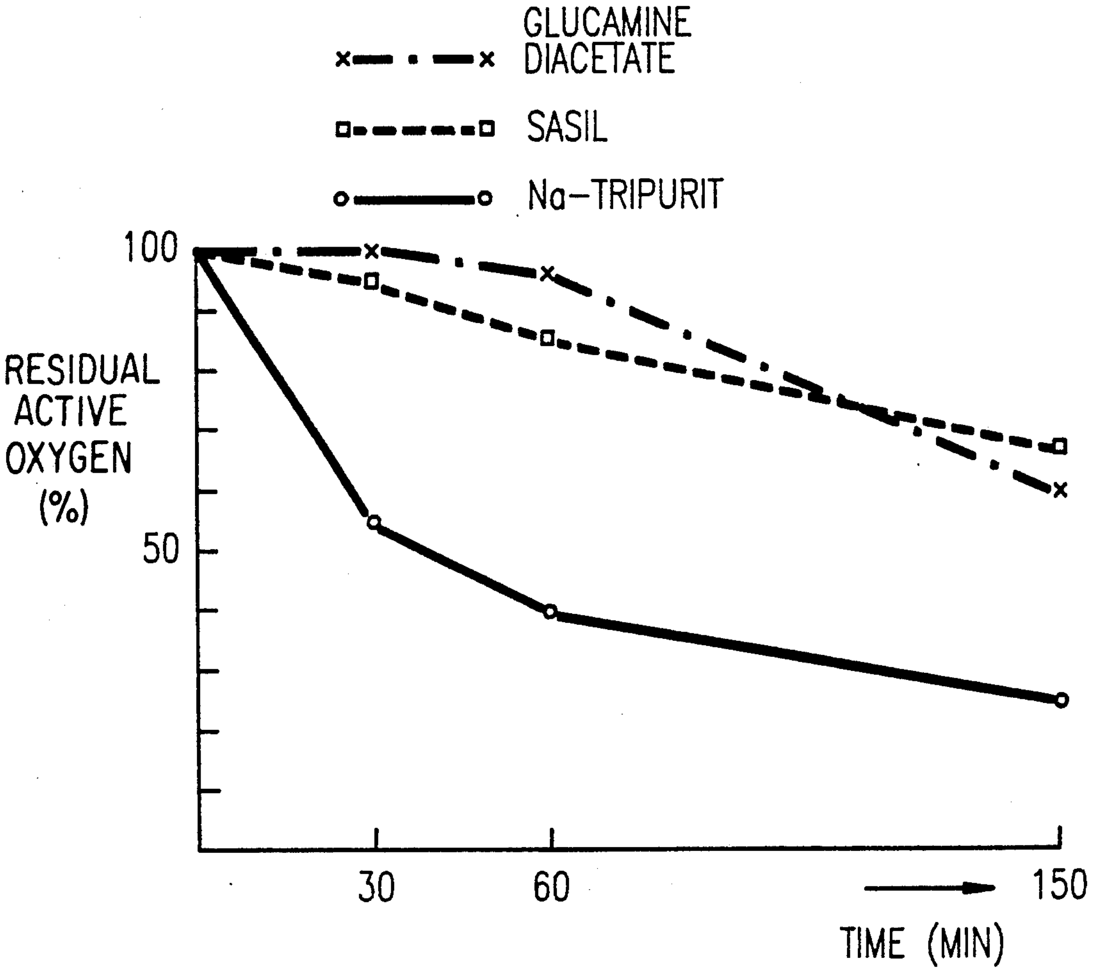

FIG. 2 is graph of residual active oxygen versus time as obtained from a test solution containing a concentration of agents of 0.77 g/liter builder, 0.62 g/liter sodium perborate.$4H_2O$ and 0.01 g/liter Fe(III) chloride. The residual active oxygen value was taken as a measure of perborate stability.

As the examples show, the inventively employed compounds are clearly superior to the ecologically unobjectionable zeolites (SASIL®) in the important characteristics, e.g., detergency, effect on incrustation, and perborate stability.

Although the triphosphate is the best as a builder, some of the properties of the inventively employed compounds are superior to those of the triphosphate, i.e., Hampshire Ca-binding test and perborate compatibility, and some are nearly as good, i.e., incrustation and detergency.

The inventively employed types of compounds do not lead to eutrophication. Accordingly, their use in detergents and cleaning agents represents a true advance of the art, and a surprising one as well.

Obviously, numerous modifications and variations of the present invention are possible in light of the above teachings. It is therefore to be understood that within the scope of the appended claims, the invention may be practiced otherwise than as specifically described herein.

What is claimed as new and desired to be secure by Letters Patent of the U.S. is:

1. A detergent or cleansing composition, comprising: a combination of at least one surfactant with from 2–60 wt.%, based on the weight of the composition, of a builder consisting of a polyhyroxyalkylamine-N,N-dialkylcarboxylic acid or a salt thereof of the formula:

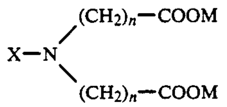

wherein X is 1 -deoxyerythrityl, 1-deoxyarabityl, 1-deoxyxylityl, 1-deoxysorbityl, 2-deoxysorbit-2-yl, 1-deoxymannityl, 2-deoxymannit-2-yl, 1-deoxygalactityl, 1-deoxy-4-glucosidosorbityl, 1-deoxy-4-galactosidosorbityl, 2-deoxy-4-glucosido-sorbit-2-yl, 2-deoxy-4-glucosidomannit-2-yl, 1-deoxy-4-maltoglucosido-sorbityl, 1-deoxy-4-oligoglucosido-sorbityl, or 1-deoxy-4-polyglucosidosorbityl, M is hydrogen, ammonium or an alkali metal ion and n is an integer of from 1 to 3.

2. The composition of claim 1, wherein X is 1-deoxysorbityl.

3. A detergent or cleansing composition, comprising: a combination of at least one surfactant with from 2–60 wt.%, based on the weight of the composition, of a builder consisting of a polyhydroxyalkylamine-N,N-dialkylcarboxylic acid or a salt thereof of the formula:

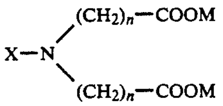

wherein X is a group containing a polyhydroxyalkyl group of 3 to 7 carbon atoms glycosidically bonded to a mono-, di- or oligosaccharide, M is hydrogen, ammonium or an alkali metal ion and is an integer of from 1 to 3.

4. A detergent or cleansing composition, comprising: a combination of at least one surfactant with from 2–60 wt.%, based on the weight of the composition, of a builder consisting of a polyhydroxyalkylamine-N,N-dialkylcarboxylic acid or a salt thereof selected from the group consisting of glucamine diacetate, erythramine diacetate, arabinamine diacetate, xylamine diacetate, mannamine diacetate, galactamine diacetate, 2-deoxysorbit-2-ylamine diacetate, 2-deoxymannit-2-ylamine diacetate, 4-glucosidoglucamine diacetate, 4-galactosidoglucamine diacetate, 2-deoxy-4-glucosido-sorbit-2-ylamine diacetate, 2-deoxy-4-glucosido-mannit-2-ylamine diacetate, 4-maltoglucosido-glucamine diacetate, 4-oligoglucosidoglucamine diacetate, or 4-polyglucoside-glucamine diacetate.

5. A detergent or cleansing composition, comprising: a combination of at least one surfactant with from 2–60 wt.%, based on the weight of the composition of a perborate stabilizing builder consisting of a polyhydroxyalkylamine-N,N-dialkylcarboxylic acid or a salt thereof of the formula:

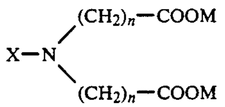

wherein X is a group containing a polyhydroxyalkyl group of 3 to 7 carbon atoms glycosidically bonded to a monodi- or oligosaccharide, M is hydrogen, ammonium or an alkali metal ion and n is an integer of from 1 to 3.

* * * * *